US007909787B2

(12) United States Patent
Ravikumar

(10) Patent No.: US 7,909,787 B2
(45) Date of Patent: Mar. 22, 2011

(54) RECONFIGURABLE HEEL ELEVATOR

(76) Inventor: Sundaram Ravikumar, Briarcliff Manor, NY (US)

(*) Notice: Subject to any disclaimer, the term of this patent is extended or adjusted under 35 U.S.C. 154(b) by 0 days.

(21) Appl. No.: 11/356,692

(22) Filed: Feb. 17, 2006

(65) Prior Publication Data

US 2007/0095353 A1 May 3, 2007

Related U.S. Application Data

(60) Provisional application No. 60/730,766, filed on Oct. 27, 2005.

(51) Int. Cl.
*A61F 5/00* (2006.01)

(52) U.S. Cl. ................. 602/13; 602/23; 602/26; 602/27

(58) Field of Classification Search ................ 602/5, 13, 602/19, 23, 26, 27; 128/882, DIG. 20
See application file for complete search history.

(56) References Cited

U.S. PATENT DOCUMENTS 3,939,829 A 2/1976 Spann
3,946,451 A 3/1976 Spann
4,071,031 A * 1/1978 Lowman ....................... 607/114
4,186,738 A 2/1980 Schleicher
4,197,845 A 4/1980 Browning
4,266,298 A * 5/1981 Graziano ............................ 2/22
4,399,815 A 8/1983 Bachorik
4,409,975 A 10/1983 Simhoni
D274,264 S * 6/1984 Andersson ................... D24/190
4,730,610 A 3/1988 Graebe
4,944,060 A 7/1990 Peery
4,977,891 A * 12/1990 Grim ............................... 602/27
5,085,214 A 2/1992 Barrett
5,226,245 A * 7/1993 Lamont ........................... 36/9 R
5,328,445 A * 7/1994 Spahn et al. .................... 602/13
5,412,822 A 5/1995 Kelly
5,431,624 A 7/1995 Saxton
5,449,339 A 9/1995 Drennan
5,476,105 A 12/1995 Toth
5,489,259 A 2/1996 Jacobs
5,666,681 A 9/1997 Meyer
5,765,564 A 6/1998 Ewing
5,839,139 A 11/1998 Fink
5,876,364 A 3/1999 Herbst
5,913,841 A 6/1999 Lamont (Continued)

*Primary Examiner* — Michael A. Brown
(74) *Attorney, Agent, or Firm* — Edwards Angell Palmer & Dodge LLP

(57) ABSTRACT

A method and apparatus for eliminating or otherwise reducing or mitigating pressure on an individual's heel while the leg is in an extended position, while allowing for ambulation without completely removing the device. An apparatus comprises a support member configured to be attached to a lower leg portion of an individual between the calf and heel region, the support member having an inner surface portion to be disposed facing the leg when attached thereto, and having an opposite outer surface; and a reconfigurable elevation member configured (i) to be disposed at the outer surface of the support member such that when the support member is attached to the lower leg portion of the individual the elevation member is selectively capable of providing elevation of the heel from an underlying surface in the event that the lower leg portion is extended above the underlying surface, and (ii) to be reconfigured for ambulation without removing said support member from the lower leg. In some implementations, the reconfigurable elevation member is integral with the support member and is inflatable and deflatable. In other implementations, the reconfigurable elevation member is removably attachable to the support member, and may be removed for ambulation while the support member remains securely in place such that the elevation member may be reattached thereto.

19 Claims, 5 Drawing Sheets

U.S. PATENT DOCUMENTS

| | | | | |
|---|---|---|---|---|
| 5,957,872 | A | 9/1999 | Flick | |
| 5,957,874 | A | 9/1999 | Klein | |
| 5,997,491 | A | 12/1999 | Harris | |
| 6,149,613 | A | 11/2000 | Klein | |
| 6,151,739 | A | 11/2000 | Meyer | |
| 6,175,979 | B1 | 1/2001 | Jackson | |
| 6,260,221 | B1 | 7/2001 | Grabell | |
| 6,351,863 | B1 | 3/2002 | Meyer | |
| 6,572,573 | B1 * | 6/2003 | Klein | 602/23 |
| 6,634,045 | B1 | 10/2003 | DuDonis | |
| 2001/0016960 | A1 | 8/2001 | Grabell | |
| 2002/0032485 | A1 | 3/2002 | Flam | |
| 2003/0182727 | A1 | 10/2003 | DuDonis | |
| 2005/0060808 | A1 | 3/2005 | Shaw | |
| 2005/0107728 | A1 | 5/2005 | Vetters | |

* cited by examiner

RECONFIGURABLE HEEL ELEVATOR

This application claims the benefit of US Provisional Application No. 60/730,766, filed Oct. 27, 2005, which is incorporated herein by reference in its entirety.

BACKGROUND OF THE INVENTION

1. Field of the Invention

The present invention relates generally to preventing, treating, and/or relieving decubitus ulcers and, more particularly, to a device that reduces or eliminates heel pressure while the leg is extended, and that allows for and does not impede ambulation while the device is in place.

2. Background Information

Because of its thin layer of subcutaneous tissue between the skin and bone, the heel is the second most common site for pressure ulcer development (after the sacrum). Heel ulcers are costly and, if not treated promptly and properly, may lead to osteomyelitis and even limb amputation. Pressure ulcers of the heel may occur in individuals who for any reason spend extended periods of time in bed, and/or who may suffer from certain diseases or ailments making them prone to ulcers even without extended bedrest. For instance, heel ulcers often occur in patients with immobile legs due to health care problems such as fractured hips, joint replacement surgery, spinal cord injury, Guillain-Barré syndrome, or stroke, who do not move their legs because of paralysis, weakness, or pain. Diabetic patients are also susceptible to heel ulcers, as these patients may not feel foot pressure or injuries because of peripheral neuropathy, increasing the likelihood for heel ulcers even without extended bedrest or leg elevation. Further, immobile diabetic patients may have trouble moving their legs, thus exacerbating the decubitus conditions that cause heel ulcers. Patients who have leg spasms, or who are otherwise confused, may rub their heels on the bed and abrade the heel. Patients may also dig their heels into the mattress to keep from sliding down in bed, causing further pressure injury.

Effective heel ulcer treatment and prevention involves reducing pressure, friction, and shear on the heel; separating and protecting the ankles; maintaining heel pressure reduction or suspension; and preventing footdrop, even under patient movement. The apparatus should also be comfortable for the patient, easy for the caretakers to use, and permit repositioning without increasing pressure in other areas. While there are quite a few devices and techniques currently being used, none of them are able to adequately address these and other considerations for effective heel ulcer treatment and prevention.

One bedside technique widely used by caretakers is positioning a pillow, rolled towel, or folded bath blanket under the lower leg region to elevate or suspend the foot off the bed to avoid contact of the heel with the bed. In this case, the towel should be placed under the calf and not under the Achilles tendon, as using a rolled towel under the Achilles tendon to lift the leg for more than a day or two may injure the Achilles tendon. Improper positioning and/or excessive height of such improvised elevating devices may hyper-extend the knee. Such improvised bedside techniques, therefore, are evidently not well controlled, and may not only be ineffective in preventing heel pressure, but also may lead to other injuries.

Numerous leg elevating products are marketed that act like special-purpose pillows or cushions upon which the leg and/or foot rests. Such products may be well suited for patients with immobile legs, such as those recovering from hip and knee surgery or stroke. Because these devices generally are not securely attached to the patient, they typically do not adequately protect the patient's heel from pressure, abrasion, and/or shear as the patient moves or changes body position. Accordingly, if the patient is at risk for moving her leg off the device, or if her leg needs to be elevated longer than a few days, then it may be better to use a product that stays on the foot during movement.

Many heel protection devices that are attachable to the leg and/or foot are marketed. Although such a device may be selected for use on patients who are able to move their leg and who thus may be able to ambulate, typically the device itself prevents or otherwise impedes ambulation, and generally must be entirely removed for ambulation, and then repositioned and reattached when the patient returns to the bed. Additionally, many of these devices encase or enclose the heel, thus not providing for the elimination of heel pressure, and not providing much advantage other devices and techniques for preventing heel abrasion by reducing friction from shearing and rubbing, such as various moisturizers, socks, and dressings (such as films or hydrocolloids).

Therefore, in view of the background information presented hereinabove, the need is manifest for advances in decubitus ulcer prevention and treatment, and particularly for the prevention and treatment of heel ulcers.

SUMMARY OF THE INVENTION

Various embodiments of the present invention provide such advancements and overcome the above mentioned and other problems and limitations of the background art, by providing a method and apparatus for eliminating or otherwise reducing or mitigating pressure on an individual's heel while the leg is in an extended position, while allowing for ambulation without completely removing the device.

In accordance with an aspect of the present invention, an apparatus comprises a support member configured to be attached to a lower leg portion of an individual between the calf and heel region, the support member having an inner surface portion to be disposed facing the leg when attached thereto, and having an opposite outer surface; and a reconfigurable elevation member configured (i) to be disposed at the outer surface of the support member such that when the support member is attached to the lower leg portion of the individual the elevation member is selectively capable of providing elevation of the heel from an underlying surface in the event that the lower leg portion is extended above the underlying surface, and (ii) to be reconfigured for ambulation without removing said support member from the lower leg.

In accordance with another aspect of the present invention, the reconfigurable elevation member may include an inflatable and deflatable bladder integral with the support member. The reconfigurable elevation member may be reconfigured for ambulation by deflating the bladder. The inflatable bladder may be apportioned into a plurality of pneumatically coupled regions separated by at least one baffle. The support member may include an adhesive portion for attachment to the lower leg.

In accordance with a further aspect of the present invention, the support member includes opposing lateral portions disposed adjacent to opposite lateral sides of the lower leg relative to the saggital plane, and further comprising for each lateral portion at least one lateral cushion member removably attachable to or integral to the lateral portion. At least one lateral cushion member may be inflatable and deflatable.

In some implementations, the support member may comprise a semi-rigid plastic spine and a foam member attached to the inner surface of the support member, and wherein the inflatable and deflatable bladder is disposed at the outer surface of the semi-rigid plastic spine.

In accordance with still other embodiments of the present invention, an apparatus comprises a support member configured to be attached to a lower leg portion of an individual between the calf and heel region, the support member having an inner surface portion to be disposed facing the leg when attached thereto, and having an opposite outer surface; and a reconfigurable elevation member that is removable attachable to the support member and is configured (i) to be disposed at the outer surface of the support member such that when the support member is attached to the lower leg portion of the individual the elevation member is selectively capable of providing elevation of the heel from an underlying surface in the event that the lower leg portion is extended above the underlying surface, and (ii) to be reconfigured for ambulation without removing said support member from the lower leg. Upon detaching the reconfigurable elevation member from the support member for ambulation, the apparatus does not impede ambulation.

In accordance with some aspects of such other embodiments, the reconfigurable elevation member includes a cushion member that, upon attaching the reconfigurable elevation member to the support member, is disposed at the outer surface of the support member such that when the support member is attached to the lower leg portion of the individual, the cushion member provides elevation of the heel from an underlying surface in the event that the lower leg portion is extended above the underlying surface. The cushion member may provide elevation of the heel sufficient to spatially separate the heel from the underlying surface. The cushion member may be implemented as at least one of a fluid filled member that is not adapted for deflation, and a preformed cushion member that is not adapted for deflation.

In accordance with other aspects of such other embodiments, the reconfigurable elevation member includes at least one inflatable and deflatable bladder that, upon attaching the reconfigurable elevation member to the support member, is disposed at the outer surface of the support member such that when the support member is attached to the lower leg portion of the individual, the bladder provides for adjustable elevation of the heel from an underlying surface in the event that the lower leg portion is extended above the underlying surface, and wherein the bladder is inflatable by a predetermined fluid. The predetermined fluid may be air or other gaseous, liquid, gel, or other fluid-like material.

In accordance with some aspects of such embodiments, the inflatable and deflatable bladder may be apportioned into a plurality of pneumatically coupled regions separated by at least one baffle. The pneumatically coupled regions may include a plurality of lateral baffle portions configured to be disposed adjacent to opposite lateral sides of the lower leg relative to the saggital plane upon attaching the inflatable bladder to the support member.

In accordance with some implementations, the reconfigurable elevation member is removably attachable to the support member by a hook and loop fastener, such as Velcro® brand Hook and Loop Fasteners available from Velcro USA Inc. located in Manchester New Hampshire. Additionally, the support member may comprise a backing layer material and a foam member attached to the inner surface of the backing layer material.

In accordance with still other aspects of the present invention, methods are provided for preventing or treating heel ulcers or otherwise mitigating or eliminating heel pressure by attaching the support member to an individual's lower leg at the calf area just above the ankle, and inflating a bladder integral to the support member. When the patient is in a supine position, the bladder assembly is in contact with the surface of the bed and elevates the heel thereby eliminating the contact of the heel with the surface of the bed. When the patient needs to move around, the bladder can be deflated.

In accordance with still other aspects of the present invention, methods are provided for preventing or treating heel ulcers or otherwise mitigating or eliminating heel pressure by attaching a support member to an individual's lower leg at the calf area just above the ankle, and attaching a removably attachable cushioning member thereto. The cushioning member may be inflatable and deflatable, in which case the cushioning member is inflated before or after attachment to the support member. When the patient is in a supine position, the bladder assembly is in contact with the surface of the bed and elevates the heel thereby eliminating the contact of the heel with the surface of the bed. When the patient needs to move around, the cushion member can be detached. The cushion member can be reattached again if required. The cushion may comprise a bladder assembly including three air filled bladders made of PVC and joined at the sides. Hook and loop fasteners may be used to attach the bladder assembly to the support member.

It will be appreciated by those skilled in the art that the foregoing brief description and the following detailed description are exemplary and explanatory of this invention, but are not intended to be restrictive thereof or limiting of the advantages which can be achieved by this invention. Thus, the accompanying drawings, referred to herein and constituting a part hereof, illustrate preferred embodiments of this invention, and, together with the detailed description, serve to explain the principles of this invention.

BRIEF DESCRIPTION OF THE DRAWINGS

Additional aspects, features, and advantages of the invention, both as to its structure and operation, will be understood and will become more readily apparent when the invention is considered in the light of the following description made in conjunction with the accompanying drawings, wherein.

DETAILED DESCRIPTION OF EMBODIMENTS OF THE INVENTION

As will be understood and more fully appreciated from the ensuing description, embodiments of the present invention are configured for attachment to the lower leg to provide for reducing or eliminating pressure on the heel region of the foot when the leg or foot is positioned such that the heel is in contact with an underlying surface (e.g., a bed) or would be in contact with an underlying surface but for the presence of the device. That is, as will be further understood below, while embodiments of the present invention may be implemented to sufficiently elevate the foot to provide for spatial separation of the heel from an underlying surface that the heel would otherwise rest upon, such and other embodiments of the present invention need not be used to provide such spatial separation of the heel, but rather may be advantageously used to reduce pressure on the heel even if the heel is in contact with an underlying surface. Additionally, even when the foot may be cantilevered over the end of a bed or other supporting structure, embodiments of the present invention may be used to provide cantilever elevation and support, and to prevent or otherwise reduce pressure on the heel region as the individual moves while the heel is originally in a cantilevered position. Further, while embodiments of the present invention are securely attached to the individual to ensure proper operation of the device, these devices are easily reconfigurable at the bedside to allow the individual to ambulate without being impeded by the device.

Figure 1A:
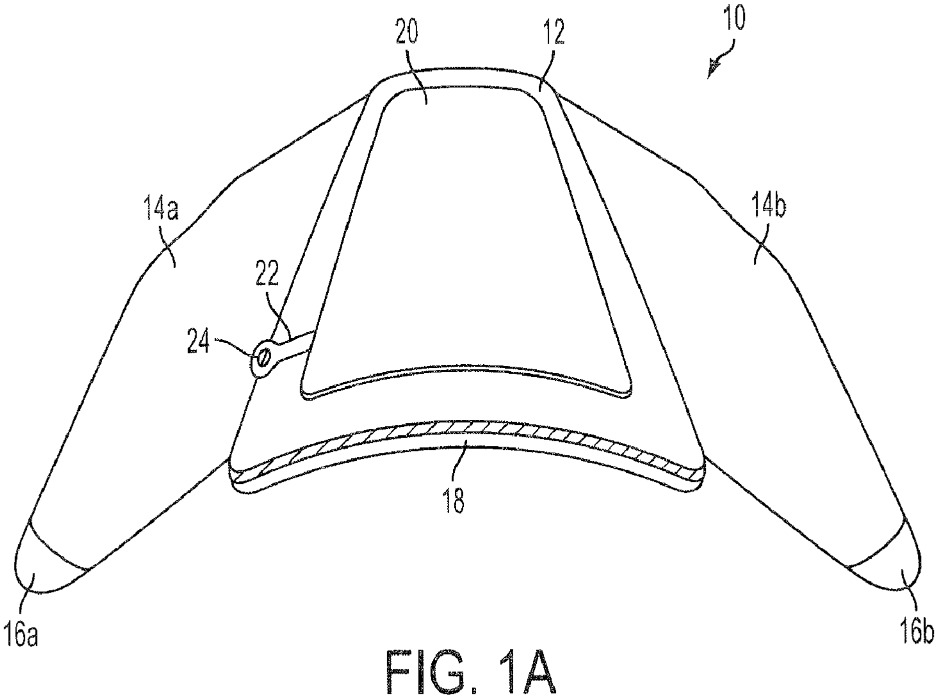
FIGS. 1A and 1B illustrate isometric views of a heel elevation device, in accordance with an embodiment of the present invention.
Figure 1B:
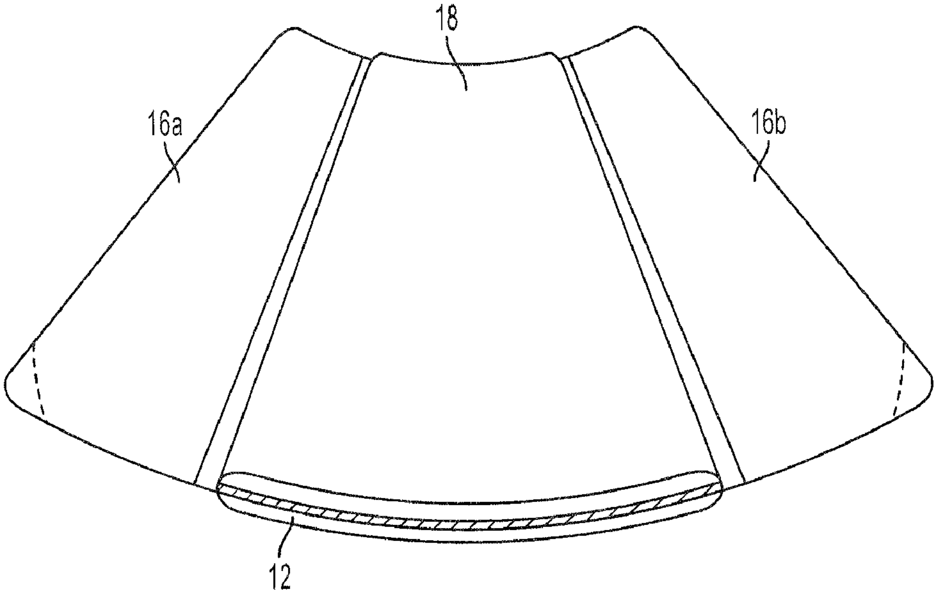

In accordance with an illustrative embodiment of the present invention, FIGS. 1A and 1B depict perspective views of a reconfigurable heel elevator implemented as an inflatable/deflatable heel elevation device 10 comprising backing or spine 12, extensions 14*a* and 14*b*, peelable barriers 16*a* and 16*b*, foam layer 18, inflatable bladder 20, lumen or tube 22, and valve 22. In this illustrative embodiment, backing/spine 12 is made of plastic and is semi-rigid, being contoured to conform to the shape of the lower leg between the calf and ankle region, having a concave inner (i.e., leg-facing) surface and being laterally wider towards the upper part of the leg (the proximal end) and tapering towards the lower part of the leg (the distal end). In some embodiments, backing/spline 12 may be made of various materials (e.g., plastic, polymer, rubber, resin, fabric, etc.) with varying degrees of flexibility; for instance, backing/spline 12 may alternatively be made of neoprene or similar material that is flexible or bendable by hand such that backing/spine 12 may be wrapped around or otherwise conformed to the lower leg region of the patient.

According to the embodiment depicted in FIGS. 1A and 1B, two extensions 14*a* and 14*b* made of a flexible material, such as polyurethane/PVC, extend from the lateral edges of backing/spine 12. Extensions 14*a* and 14*b* may be integrally formed with backing/spine 12, or may otherwise be attached thereto. The inner (i.e., leg-facing) surfaces of extensions 14*a* and 14*b* include an adhesive, which is covered by peelable barriers 16*a* and 16*b*. The adhesive may be any of various well-known medical adhesives for adhering to the skin (e.g., acrylic polymer), and in some embodiments the construction and technology of the extensions 14*a* and 14*b*, the adhesive, and peelable barriers 16*a* and 16*b* may be similar to that of adhesive bandages or protective strips.

A thin foam layer 18 (e.g., one-quarter inch foam) is attached to, and contoured in conformity with, the inner surface (i.e., leg facing, concave surface) of backing/spine 12. In this embodiment, foam layer 18 is provided for additional patient comfort and improved comformity to the leg, as opposed to having semi-rigid backing/spine 12 contact the leg directly. In alternative implementations, such as embodiments employing a softer and/or flexible backing, foam layer 18 may be eliminated, and the backing material may directly contact the leg. Additionally, as further discussed hereinbelow, it is understood that elevation device 10 may be implemented in a variety of configurations, and may be secured to an individual's leg by any of a variety of fastening mechanisms that may be employed in addition, or as an alternative, to an adhesive.

As depicted in FIG. 1A, inflatable bladder 20 (shown in the deflated state) is attached to the outer surface (facing away from the leg when in place) of backing/spine 18, and may be made of polyurethane or other plastic or polymer material. In some embodiments, rather than bladder 20 being an inflatable closed surface that is attached to backing/spine 18, the outer surface of backing/spine 18 may form part of the inner, air-containing surface of bladder 20. Bladder 20 has a valve 24 through which air can be pumped to inflate the bladder, and, in this embodiment, valve 24 is coupled to bladder 20 via a lumen or tube 22, which is also attached to the outer surface of backing/spine 18. As will be appreciated, valve 24 may be positioned at any location on or relative to bladder 20, and in this embodiment valve 24 is positioned laterally (by means of tube 22) and proximally such that the valve is easily accessible for inflation/deflation and does not impede or interfere with the patient, create a pressure point, or otherwise cause patient discomfort. A manually operated squeeze bulb, electrically powered mechanical pump, or other source of compressed air may be used to inflate bladder 20. Valve 24 may be a self-sealing, pressure-type valve that automatically seals upon removal of inflation pressure, and may additionally or alternatively provide for deflation without attaching a pumping mechanism for evacuation. In some embodiments, bladder 20 may be implemented for filling or inflation with a fluid other than other than air.

Bladder 20 may be formed and dimensioned to provide a desired profile and volumetric shape when inflated. For instance, in the embodiment shown in FIG. 1A, the outer contour of bladder 20 along the surface of backing/spine 18 has a generally trapezoidal shape that is similar to the generally trapezoidal shape of backing/spine 18. Additionally, in this embodiment, bladder 20 is formed such that upon inflation the displacement between the outer surface of the bladder and the outer surface of backing/spine 18 in a direction normal to the outer surface of backing/spine 18 monotonically increases from the proximal end (end near the calf when in position) to the distal end (end near the heel when in position).

Figure 2:
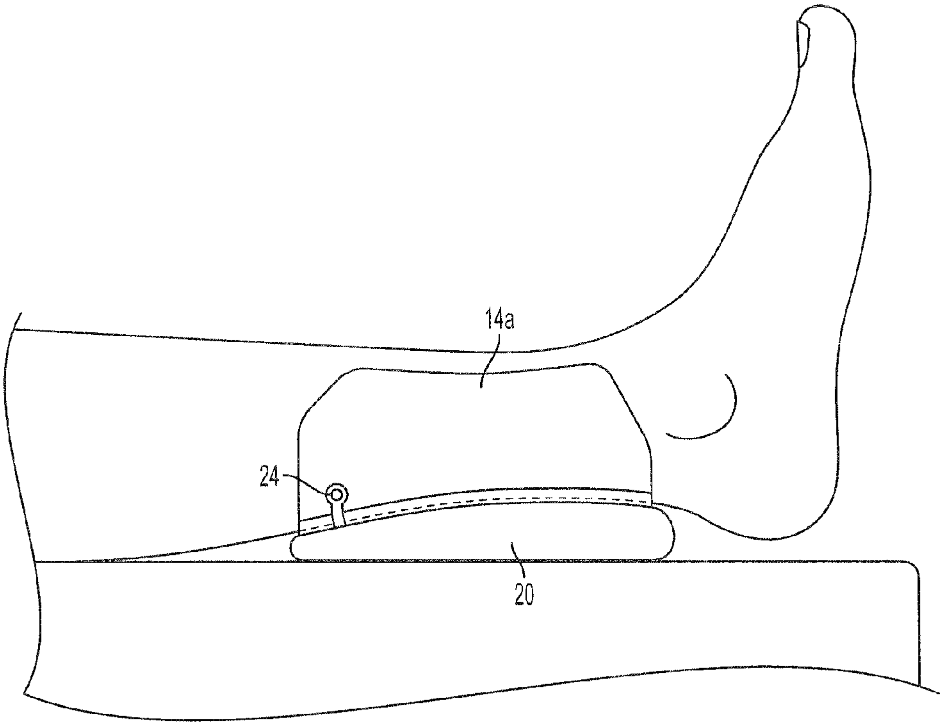
FIG. 2 schematically depicts a side view of the heel elevation device of FIGS. 1A and 1B attached to an individual's leg, in accordance with an embodiment of the present invention.

Such a profile is shown in FIG. 2, which depicts a side view of heel elevation device 10 attached to a patient's leg. As may be understood from this side view, the cross sectional profile in the sagittal plane has a generally trapezoidal, tapered shape that generally complements the contour of the adjacent rear leg portion such that the outer surface (posterior surface) of bladder 20 is generally parallel to the shin. Also, as embodied, the maximum displacement between the outer and inner surfaces of the bladder (i.e., when the bladder is fully inflated) is great enough to sufficiently elevate the patients heel such that the heel is spaced away from an underlying surface 29 (e.g., a bed), which surface the patient's heel would rest upon but for the elevation provided by heel elevation device 10. By way of example, such maximum displacement may be about two to three inches. It is understood, however, that even if the patient's heel or foot is cantilevered off the edge of an underlying surface (e.g., bed), heel elevation device 10 is still useful for preventing, for example, possible abrasions or shear, possible digging of the heels in the bed, heel pressure in the event the patient moves such that the foot or leg is no longer cantilevered, as well as for reducing or preventing pressure on the Achilles tendon and/or reducing or preventing other concentrated pressure that may affect circulation.

An illustrative technique for applying and using inflatable/deflatable heel elevation device 10 is as follows. Heel elevation device 10 may be positioned near and/or against the patient's lower leg, between the calf and ankle region. Then, peelable barriers 16*a* and 16*b* are peeled away to expose the underlying adhesive on the inner surfaces of extensions 14*a* and 14_b_, which are then pressed against the patient's leg, thus adhering heel elevation device 10 to the patient's leg (with foam layer 18 against the patient's leg). Then, in the case that the patient is or will be in a supine position or other position where the patient's leg is extended so as to rest upon an underlying surface, and in the case that the case that bladder 20 is in a deflated state, or additional inflation is otherwise desired, bladder 20 is inflated to a desired level of inflation (e.g., inflation pressure) to provide the desired heel elevation, cushioning/firmness, and/or stability. As will be appreciated, the elevation height may be adjustable, based on the volume (and hence pressure) of air pumped into the bladder. In the event that the patient intends to ambulate, bladder 20 may be deflated to avoid, for example, rubbing of the bladder against the other leg (e.g., the occurrence and amount of which depends on the particular design of the bladder(s)), or any other inconvenience, impediment, or awkwardness in ambulation.

In this illustrative embodiment, the semi-rigidity of backing/spline 12 may also prevent or mitigate excessive inward pressure against the back of the leg as the bladder is inflated, which pressure could affect circulation, or excessively strain the adhesive coupling to the leg (e.g., causing discomfort, or possibly causing the extensions to peel away from the leg). Such prevention or mitigation of inward pressure may alternatively or additionally be accomplished by the design of the bladder itself (e.g., designing the bladder wall material and/or configuration such that it inflates predominantly or entirely outwardly in the posterior direction). It is understood, however, that such prevention or mitigation of inward pressure is not a necessary feature for implementing embodiments of the present invention. In some embodiments, at least a certain degree of inward inflation is advantageous for distributing the pressure over the back of the leg, conforming to the leg, and/or providing stable support (e.g., lateral support) for elevating the heel and reducing heel pressure.

In some embodiments, the outer surface of either or each extension piece 14_a_ and 14_b_ may be implemented with an integrally formed and/or irremovably attached inflatable/deflatable bladder, as may be desirable to further prevent and/or mitigate heel pressure, friction or shearing, by providing additional lateral support, cushioning and elevation (e.g., in the case the patient lies on his side). These bladders may be pneumatically isolated from bladder 20, and may have separate valves for individual inflation/deflation, or may be pneumatically coupled to each other (e.g., by a tube) such that they may be inflated/deflated through a common valve. One or both of these bladders may be inflated when the leg is extended (e.g., the patient is in the supine position), and one (e.g., the bladder on the instep side of the sagittal plane; i.e., the one facing the opposing leg) or both may be deflated for ambulation. In some embodiments, bladder 20 may be configured such that it does not impede ambulation even if inflated (e.g., the lateral extent of bladder 20 is limited), and thus only one or both of the lateral bladders may be deflated for ambulation. In alternative embodiments, the lateral bladders may be removably attachable (e.g., by hook and loop fasteners, snaps, etc.) to extensions 14_a_ and 14_b_, and, as such, need not be inflatable/deflatable, but may, for example, be implemented as preformed and/or prefilled (e.g., air or other fluid) cushioning member.

In still other embodiments, rather than using an inflatable/deflatable bladder 20 at the bottom, outer surface of the heel elevation device, an uninflatable/undeflatable cushioning/elevation member (e.g., foam, or a fluid filled cushion) may be used, provided it provides sufficient elevation for mitigating and/or eliminating heel pressure, and is configured such that it does not impede ambulation. In such embodiments, lateral bladders (e.g., (i) removable and inflatable/deflatable or not inflatable/deflatable, or (ii) integral/fixed and inflatable/deflatable) are advantageously included to provide additional lateral support and stability, as the bottom bladder generally will require a narrower lateral extent to avoid impeding ambulation. As noted above, in the case that these lateral bladders are removable, it is not necessary that they be deflatable; for instance, they may be implemented using any of a variety of cushioning materials (e.g., foam), including air, gel, or other fluid filled cushions. It is noted, however, that inflatable/deflatable bladders (e.g., for the bottom/posterior cushioning member as well as for the lateral cushioning members) are well suited for providing adjustability of elevation and cushioning/firmness, as well as for evenly distributing/redistributing pressure and conforming to the patients leg, even under dynamic load conditions (e.g., resulting from patient movements that may change the load conditions).

As understood and indicated by the foregoing description of illustrative embodiments and variations thereof, cushioning members (posterior and/or lateral) may have a variety of shapes or profiles. For instance, in the deflated state, various embodiments of posterior bladder 20 may have a generally triangular (e.g., isosceles triangle) or generally trapezoidal (e.g., isosceles trapezoid) shape in the lateral plane (e.g., when the heel elevation device 10 is laid flat on a planar surface), with the base or wider base portion being disposed such that it will be proximal to the knee when the heel elevation device is attached to an individual's leg. Such a triangular or trapezoidal deflated bladder is configured such that upon inflation the bladder will have a generally conical shape, with the narrower apex of the conical bladder being towards the top of the leg (i.e., the proximal end of the bladder relative to the knee), and the wider base of the conical bladder being toward the bottom of the leg (i.e., the distal end relative to the knee; proximal to the ankle/heel), such that the fluid filled (e.g., air-filled) cross sectional area increases from the calf towards the heel.

It may also be understood that in some embodiments, more than one separately inflatable posterior bladder may be provided along the length (longitudinally) between the proximal and distal ends. The cross sectional elevation profile in the sagittal plane (i.e., elevation along the longitudinal direction) may thus be adjusted by separately adjusting the pressure of each posterior bladder provided. Alternatively, or additionally, a bladder may be apportioned into multiple sections that are commonly inflated, but have different shapes or contain different volumes of fluid when the bladder is inflated. For instance, bladder 20 may be adapted to include multiple longitudinal and/or lateral sections by, for example, separating the sections with baffles that may be formed by heat sealing the outer surface of the bladder to the inner surface (e.g., the backing/spline side) along most of the extent dividing adjacent sections, but leaving an opening between adjacent sections such that fluid (air) can flow therethrough. Accordingly, upon inflation, each of the sections will be filled, but the shape/profile of each section may be determined by the baffle configuration/shape and the fluid containing volume of each section separated by the baffles.

Figure 3:
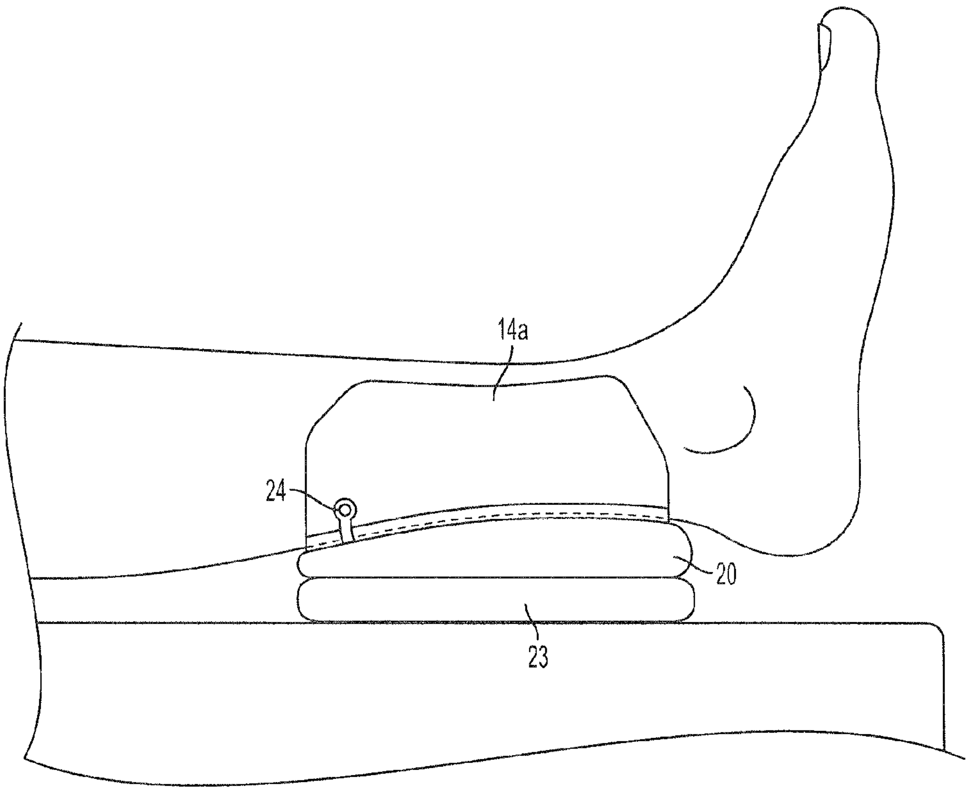
FIG. 3 schematically depicts a side view of a heel elevation device attached to an individual's leg, in accordance with another embodiment of the present invention.

As yet a further illustrative example of variations within the purview of the present invention, more than one separately inflatable bladder may be provided in the posterior direction to allow variable height adjustment and cushioning pressure by selectively filling one or more bladders. FIG. 3 schematically depicts a side view of an illustrative embodiment of a heel elevation device implementing such a variation, and having two separately inflatable/deflatable bladders 20 and 23. (For ease of reference, components similar to those in FIG. 2 are labeled with identical reference numerals). As depicted, while the first bladder 20 may have a generally trapezoidal cross-section (as in the embodiment of FIG. 2), a second bladder 23 may have a uniform cross sectional thickness in the sagittal plane. More specifically, in FIG. 3, a first bladder attached to the plastic spline when fully inflated may provide an air cushion thickness of up to about 2 inches, and a second bladder attached to the outer side of the first may also provide an air cushion thickness of up to about 2 inches when fully inflated, thus together providing for up to about 4 inches of adjustable elevation. The inner and outer bladders may be appropriately shaped, for instance, such that the anterior bladder (i.e., bladder 20) conforms to the rear of the leg, while the posterior bladder (bladder 23) provides additional elevation. In this embodiment, a separate valve (and tube/lumen) is provided for inflating/deflating bladder 23; however, it is not visible in FIG. 3, as it is symmetrically located with respect to the sagittal plane (i.e., it is laterally displaced from valve 24, on the opposite outer sidewall of extension.

In the foregoing illustrative embodiments, heel elevation device 10 is implemented such that the posterior elevation member (e.g., bladder 20) is an integral part of, or otherwise not removable from, the portion of heel elevation device that attaches to the patient. That is, once heel elevation device 10 is attached or applied to the patient, the elevation member cannot be removed from the patient without removing heel elevation device 10 itself from the patient. In accordance with further embodiments of the present invention, a heel elevation member that is disposed between the calf and heel region at the back of the leg is removably attachable to a support member that is attachable to the patient. As such, the support member may be securely attached to the patient's leg. The elevation member may be attached to the support member when the patient will be in a position requiring heel pressure mitigation or elimination, and may be removed from the support member when the patient will undergo ambulation; however, the support member may remain securely in place on the patient's leg, allowing for the elevation member to be readily attached whenever needed.

Figure 4:
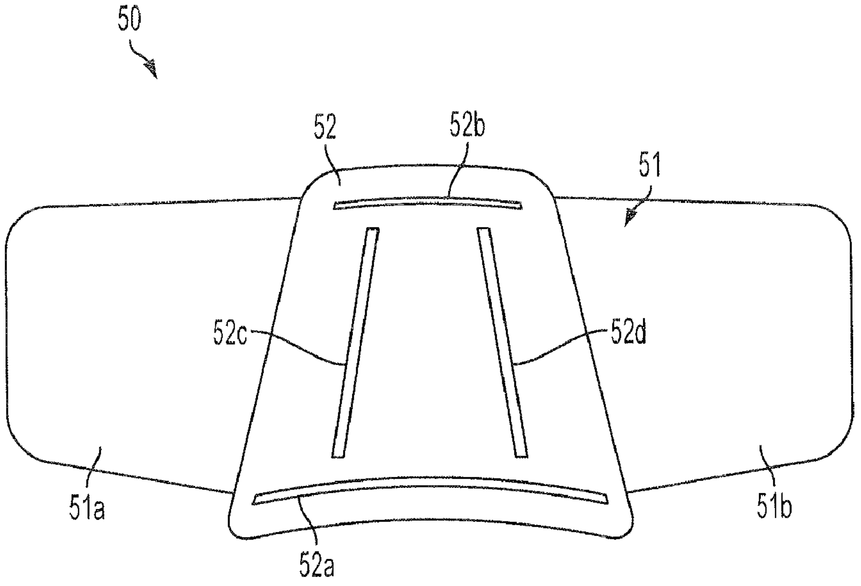
FIGS. 4 and 5 respectively depict plan views of an illustrative support member and removably attachable elevation member comprising a heel elevation device, in accordance with another embodiment of the present invention.
Figure 5:
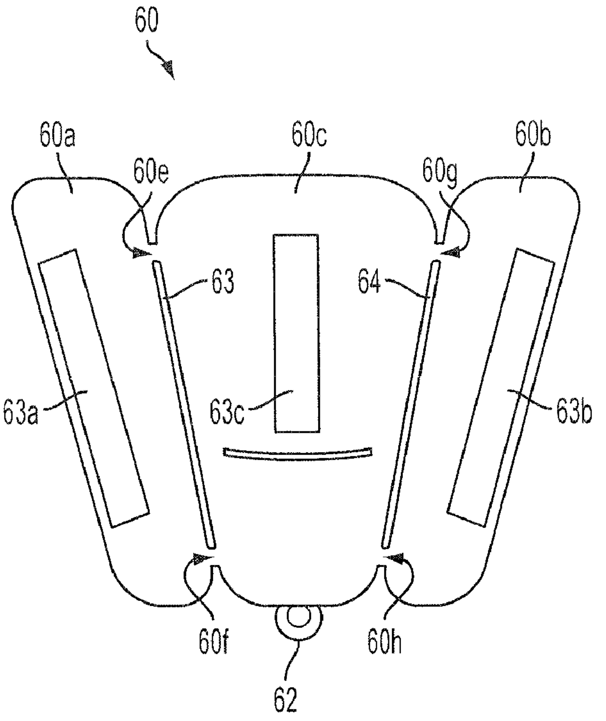

FIGS. 4 and 5 respectively depict plan views of an illustrative support member 50 and elevation member 60 comprising a heel elevation device in accordance with an embodiment of the present invention. As shown, in this embodiment, support member 50 includes backing 51 and foam member 52. Backing 51 may be made of PVC (polyvinyl chloride) or any bendable and/or elastic material (e.g., plastic, polymer, rubber, resin, neoprene, fabric, etc.) that may be wrapped about and fastened by various means to an individual's leg, while allowing elevation member 60 to be removably attached thereto. In this embodiment, similar to the embodiment of FIGS. 1-3, backing 51 includes lateral extensions 51*a* and 51*b* having a medical adhesive applied to the inner (leg facing) surface thereof and covered by peelable barriers (not shown), so that support member 50 may be attached to an individual's leg by removing the peelable barriers and adhering extensions 51*a* and 51*b* to opposing lateral sides of the leg between the calf and ankle region. As further discussed hereinbelow, it is understood that a support member may be implemented in a variety of configurations, and may be secured to an individual's leg by any of a variety of fastening mechanisms that may be employed in addition, or as an alternative, to an adhesive.

Foam member 52 is fixably attached (e.g., by adhesive) to the inner side (leg-facing side) of support member 50, and is generally contoured to conform to the human leg when the support member 50 is attached thereto. More specifically, in this embodiment, foam member 52 has a generally trapezoidal shape, the wider base portion 52*a* being the portion to be positioned toward the calf (proximal to the knee), and the narrower base portion 52*b* being the portion to be positioned toward the heel/ankle (distal relative to the knee). By way of example, the approximate length (i.e., distance along the longitudinal direction, between base portions 52*a* and 52*b*) of foam member 52 may be about 5 inches, and the width (lateral distance) of base portions 52*a* and 52*b* may be about 6 inches and 4 inches, respectively. As shown, in this embodiment, foam member 52 includes to openings or slits 52*c* and 52*d*, which are provided to facilitate conformally fitting support member 50 about the leg. Foam member 52 is thus configured to conform, and be in contact, with the back part of the lower leg between the calf and just above the heel, with extensions 51*a* and 51*b* adhering to either side of the calf and holding support member 50 in place.

Referring to FIG. 5, in this embodiment, bladder 60 comprises three sections, namely, lateral bladder sections 60*a* and 60*b*, and central bladder section 60*c*, which are together inflatable/deflatable through common valve 62. More specifically, bladder 60 is formed as an enclosed, inflatable member, including an inner surface (leg-facing surface, shown in the plan view) and an opposite outer surface (not shown), and may be made from any of a variety of materials (e.g., plastic, rubber, etc.) which may have any of varying degrees of elasticity depending on the design. As shown, attached to the inner surface of bladder sections 60*a*, 60*b*, 60*c* are hook and loop fastener segments 63*a*, 63*b*, 63*c*, which are positioned to selectively engage complementary hook and loop fastener segments (not shown) on the outer surface of backing 51 of support member 50.

In this embodiment, seam/baffle 63 (depicted as a dashed line) joins the inner and outer surfaces of bladder 60, separating lateral bladder section 60*a* from central bladder section 60*c*, except for in regions 60*e* and 60*f* which allow for fluid (air) flow between these two sections. Similarly, seam/baffle 65 (depicted as a dashed line) joins the inner and outer surfaces of bladder 60, separating lateral bladder section 60*b* from central bladder section 60*c*, except for in regions 60*g* and 60*h*, which allow for fluid (air) flow between these two sections. As such, upon inflating bladder 60 through valve 62, all three bladder sections inflate, forming a central generally oblate trapezoidal bladder 60*c*, and two generally oblate rectilinear bladders 60*a* and 60*b*. Bladder 60 may be inflated before or after attaching it to support member 50.

Figure 6:
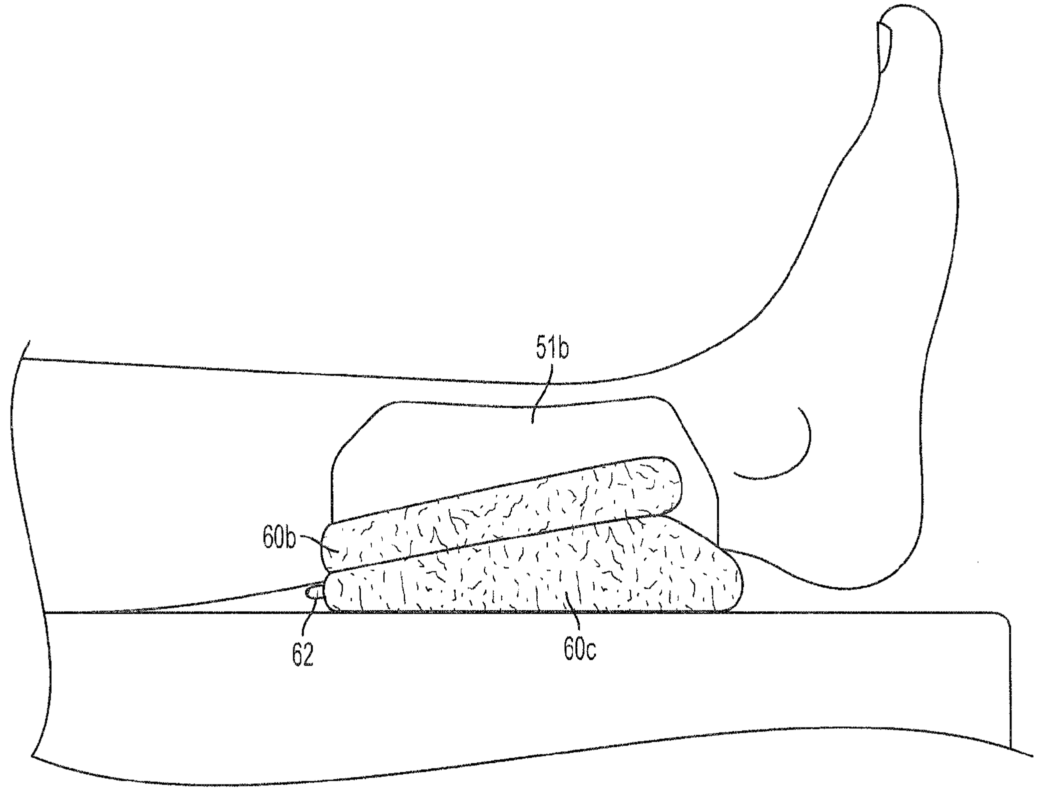
FIGS. 6 schematically depict a side view of the heel elevation device of FIGS. 4 and 5 attached to an individual's leg, in accordance with an embodiment of the present invention.

In this embodiment, in attaching the bladder assembly to the support member, the alignment of the bladder 60 is complementary to foam member 52, with the inner surfaces of lateral bladder sections 60*a* and 60*b* attaching to the outer surface of backing 51 such that they are attached to or adjacent to lateral extensions 51*a* and 51*b*, respectively, with the narrower side of bladder section 60*c* being towards the calf (towards base portion 52*a*) and the wider side being towards the heel (towards base portion 52*b*). The cross sectional shape of bladder 60*c* in the sagittal plane is roughly trapezoidal to complement the longitudinal leg profile between the calf and the ankle/heel. The central bladder 60*c* thus provides elevation at the rear/underside of the leg while the two lateral bladders 60*a* and 60*b* are generally positioned along the sides of the leg. FIG. 6 schematically depicts a sideview of a patient's leg while the patient is in a supine or recumbent position, with support member 50 attached to the patient's leg, and bladder 60 attached to support member 50 to elevate the patient's heel above a bed surface 70.

The ability to inflate/deflate bladder 60 allows for adjusting the height and cushioning pressure, while also simplifying packaging and shipping of the device. It is understood, however, that because bladder 60 is removably attachable to support 50, it need not be inflatable/deflatable; for instance, one or more of bladder sections 60*a*, 60*b*, 60*c* may be implemented using any of a variety of preformed and/or prefilled cushioning materials such as foam cushions and/or air, gel, or other fluid filled cushions. Additionally, bladder sections 60*a*, 60*b*, 60*c* need not be integral, but may be separately attachable and removable from support member 50.

The present invention has been illustrated and described with respect to specific embodiments thereof, which embodiments are merely illustrative of the principles of the invention and are not intended to be exclusive or otherwise limiting embodiments. For instance, as noted above with respect to the elevation device 10 illustrated in FIGS. 1*a*, 1*b*, and 2, and similarly with respect to the support member 50 illustrated in FIGS. 3, 4, 5, these components may be implemented in a variety of configurations, and any of a variety of fastening mechanisms may be employed in addition, or as an alternative, to an adhesive for securing the component to an individual's leg. For instance, in some alternative implementations, only a first one of the extensions may include a longitudinal adhesive strip, and the other extension may have at least a portion (or straps) having sufficient lateral extent to wrap around the entire circumference of the individual's leg and overlap the first extension and attach thereto with a fastening mechanism such as hook and loop fasteners, button(s), or straps/loops, etc. Alternatively, such buttons, straps/loops, and/or hook and loop fasteners may be used without any adhesive.

In some variations of these embodiments, it may be advantageous to include a strap that attaches to the outer surface of backing 51, or to the outer surface backing/spline 12 or extensions 14*a* and 14*b*, near both sides of the ankle, and extends longitudinally, traversing the instep and bottom of the foot, thus providing additional stability and security against motion relative to the leg. Such a strap may be removably or irremovably attached to backing 51, backing/spline 12, or extensions 14*a* and 14*b* at one or both ankle region portions.

In yet other alternative implementations, attachment or fastening mechanism between the support member 50 and bladder assembly 60 may be include one or more of buttons, hooks, adhesive, snaps, straps, etc., in addition or as an alternative to hook and loop fasteners.

Further, while particular shapes, sizes, and materials have been described for purposes of illustration, it will be recognized that any of a variety of shape or size can be used, and the materials described are not exclusive but merely illustrative. Also, as noted hereinabove, while the bladder shown is inflated with air, it will be appreciated that any other fluid or medium such as liquid or gel can be used. Moreover, as also noted, it will be understood that bladders may be configured to have multiple pneumatically independent and/or pneumatically coupled bladder sections, and may also configured to have various contours or lobulations. Additionally, while particular uses/applications of the invention have been described, it will be appreciated that the invention could be used for other applications that involve preventing contact of a body part with any other surface or with another body part. Furthermore, while this is intended to be a stand alone device, it will be appreciated that the method of using an inflatable or prefilled bladder member can be combined with other preexisting devices, such as Venodyne boots or other Intermittent Pneumatic Compression devices.

In view of the foregoing illustrative embodiments and variations thereof, it is also understood that embodiments of the present invention provide various advantages and attendant advantages, though practicing the subject matter of the present invention need not provide one or more of these advantages. Illustrative advantages include, for example, preventing, mitigating, or treating pressure ulcers of the heel while also allowing for ambulation without interference or impediment. Additionally, embodiments of the present invention ensure that the apparatus does not shift or move relative to the patient's leg. Further, embodiments of the present invention provide for heel pressure mitigation or treatment without requiring a large and/or cumbersome device.

Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. It is further noted that the terms and expressions have been used as terms of description and not terms of limitation. There is no intention to use the terms or expressions to exclude any equivalents of features shown and described or portions thereof. Additionally, the present invention may be practiced without necessarily providing one or more of the advantages described herein and/or that may be realized in some embodiments thereof. It is therefore intended that the present invention is not limited to the disclosed embodiments but should be defined in accordance with the claims that follow.

What is claimed is:

1. An apparatus comprising:

a support member configured to be attached to a lower leg portion of an individual between the calf and heel region, said support member having an inner surface portion to be disposed facing the leg when attached thereto, and having an opposite outer surface to be disposed facing away from the leg when the support member is attached thereto, wherein the support member includes a semi-rigid spine attached to the inner surface of the support member; and a reconfigurable elevation member comprising a bladder apportioned into a plurality of pneumatically coupled regions separated by at least one baffle and wherein the bladder is integral with the support member and is configured to be repeatedly inflated and repeatedly deflated, and wherein the reconfigurable elevation member is configured (i) to be disposed at the outer surface of the support member such that when the support member is attached to the lower leg portion of the individual with the inner surface portion disposed facing the leg, the bladder is capable of being inflated to provide elevation of the heel from an underlying surface in the event that the lower leg portion is extended above the underlying surface, and (ii) to be reconfigured for ambulation without removing said support member from the lower leg.

2. The apparatus according to claim 1, wherein the support member includes at least one adhesive portion for attachment to the lower leg.

3. The apparatus according to claim 1, wherein the reconfigurable elevation member is selectively capable of providing elevation of the heel by inflating the bladder to a desired level of inflation.

4. The apparatus according to claim 1, wherein the support member includes opposing lateral portions disposed adjacent to opposite lateral sides of the lower leg relative to the saggital plane, and further comprising for each lateral portion at least one lateral cushion member removably attachable to or integral to the lateral portion.

5. The apparatus according to claim 4, wherein the at least one lateral cushion member is inflatable and deflatable.

6. The apparatus according to claim 1, wherein upon the reconfigurable elevation member being reconfigured for ambulation by deflating the bladder, the apparatus does not impede ambulation.

7. The apparatus according to claim 1, wherein the reconfigurable elevation member is reconfigured for ambulation by deflating the bladder.

8. An apparatus comprising:

a support member configured to be attached to a lower leg portion of an individual between the calf and heel region, said support member having an inner surface portion to be disposed facing the leg when attached thereto, and having an opposite outer surface, wherein the support member comprises a semi-rigid plastic spine and a foam member attached to the inner surface of the support member, and wherein an inflatable and deflatable bladder is disposed at the outer surface of the semi-rigid plastic spine; and a reconfigurable elevation member configured (i) to be disposed at the outer surface of the support member such that when the support member is attached to the lower leg portion of the individual the elevation member is selectively capable of providing elevation of the heel from an underlying surface in the event that the lower leg portion is extended above the underlying surface, and (ii) to be reconfigured for ambulation without removing said support member from the lower leg.

9. An apparatus comprising:

a support member configured to be attached to a lower leg portion of an individual between the calf and heel region, said support member having an inner surface portion to be disposed facing the leg when attached thereto, and having an opposite outer surface to be disposed facing away from the leg when the support member is attached thereto, wherein the support member includes a semi-rigid spine attached to the inner surface of the support member; and a reconfigurable elevation member comprising at least one inflatable and deflatable bladder apportioned into a plurality of pneumatically coupled regions separated by at least one baffle and wherein the bladder is inflatable by a predetermined fluid, the reconfigurable elevation member configured (i) to be removably attachable to the support member such that the elevation member can be repeatedly attached to and repeatedly detached from the support member, (ii) to be disposed at the outer surface of the support member such that when the support member is attached to the lower leg portion of the individual with the inner surface portion disposed facing the leg, the elevation member is capable of being removably attached to the support member to provide adjustable elevation of the heel from an underlying surface in the event that the lower leg portion is extended above the underlying surface, and (iii) to be reconfigured for ambulation by detaching the elevation member from the support member without removing said support member from the lower leg, such that ambulation is not impeded while the support member is attached to the lower leg and the elevation member is detached from the support member.

10. The apparatus according to claim 9, wherein the reconfigurable elevation member includes a cushion member that, upon attaching the reconfigurable elevation member to the support member, is disposed at the outer surface of the support member such that when the support member is attached to the lower leg portion of the individual, the cushion member provides elevation of the heel from an underlying surface in the event that the lower leg portion is extended above the underlying surface.

11. The apparatus according to claim 10, wherein the cushion member provides elevation of the heel sufficient to spatially separate the heel from the underlying surface.

12. The apparatus according to claim 10, wherein the cushion member is implemented as at least one of a fluid filled member that is not adapted for deflation, and a preformed cushion member that is not adapted for deflation.

13. The apparatus according to claim 9, wherein the bladder is inflatable by air.

14. The apparatus according to claim 9, wherein the support member includes at least one adhesive portion for attachment to the lower leg.

15. The apparatus according to claim 9, wherein the pneumatically coupled regions include a plurality of lateral baffle portions configured to be disposed adjacent to opposite lateral sides of the lower leg relative to the saggital plane upon attaching the inflatable bladder to the support member.

16. The apparatus according to claim 9, wherein the reconfigurable elevation member includes a plurality of lateral cushion members configured to be disposed adjacent to opposite lateral sides of the lower leg relative to the saggital plane upon attaching the inflatable bladder to the support member.

17. The apparatus according to claim 16, wherein the at least one lateral cushion member is inflatable and deflatable.

18. The apparatus according to claim 9, wherein the reconfigurable elevation member is removably attachable to the support member by hook and loop fasteners.

19. The apparatus according to claim 9, wherein the support member comprises a backing layer material and a foam member attached to the inner surface of the backing layer material.

* * * * *